US00PP33897P3

(12) United States Plant Patent
Boches

(10) Patent No.: US PP33,897 P3
(45) Date of Patent: Jan. 25, 2022

(54) BLUEBERRY PLANT NAMED 'FC11-118'

(50) Latin Name: ***Vaccinium corymbosum* hybrid**
Varietal Denomination: FC11-118

(71) Applicant: Fall Creek Farm and Nursery Inc., Lowell, OR (US)

(72) Inventor: Peter Stefan Boches, Hilo, HI (US)

(73) Assignee: FALL CREEK FARM AND NURSERY INC., Lowell, OR (US)

( * ) Notice: Subject to any disclaimer, the term of this patent is extended or adjusted under 35 U.S.C. 154(b) by 0 days.

(21) Appl. No.: 17/166,597

(22) Filed: Feb. 3, 2021

(65) Prior Publication Data

US 2021/0251117 P1 Aug. 12, 2021

Related U.S. Application Data

(60) Provisional application No. 62/995,599, filed on Feb. 6, 2020.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

*Primary Examiner* — Susan McCormick Ewoldt
(74) *Attorney, Agent, or Firm* — Panitch Schwarze Belisario & Nadel LLP; Stephany G. Small; Travis W. Bliss

(57) ABSTRACT

The new blueberry plant variety 'FC11-118' is provided. 'FC11-118' is a commercial variety intended for the hand harvest fresh fruit market. The variety is produced from a cross of 'ZF05-086' (female parent, unpatented) and 'Cargo' (male parent, patented Jul. 22, 2014), which can be distinguished by its outstanding features, including extremely uniform healthy plant condition, vigor, and shape; large, uniform fruit size and distinct fruit shape; firm fruit texture; and excellent long-term cold storage performance.

6 Drawing Sheets

Latin name of the genus and species:
Genus—*Vaccinium.*
Species—*corymbosum* hybrid.
Variety denomination: The new blueberry plant claimed is of the variety denominated 'FC11-118'.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush blueberry (*Vaccinium corymbosum* L. hybrid) plant, referred to as 'FC11-118', as herein described and illustrated. The new blueberry plant variety 'FC11-118' is a commercial variety intended for the hand harvest fresh fruit market. The variety has high plant vigor, rounded growth habit, ripens mid-late season, and produces large, uniform fruit. 'FC11-118' was selected for its above average fruit quality, specifically firmness and extended cold storage performance compared to other varieties. The fruit is larger and firmer than any standard commercial variety in the same harvest window.

'FC11-118' has improved fruit firmness and storability. 'FC11-118' differs from the female parent 'ZF05-086' in that it has improved fruit firmness and storability. 'FC11-118' differs from the male parent 'Cargo' in that it has a more balanced fruit to leaf ratio, with a slightly earlier harvest season and improved firmness and storability.

Pedigree and History: The new blueberry plant originated from a cross of 'ZF05-086' (female parent, unpatented) and 'Cargo' (male parent, U.S. Plant Pat. No. 24,661 patented Jul. 22, 2014) made in Lowell, Oreg., USA in 2007. 'FC11-118' has been found to undergo asexual propagation in Lowell, Oreg. by a number of routes, such as in vitro propagation. Asexual propagation techniques in Lowell, Oreg., such as in vitro propagation, have shown that the characteristics of the new variety are homogenous, stable, and strictly transmissible by such asexual propagation from one generation to another. Accordingly, the new variety undergoes asexual propagation in a true-to-type manner.

The new blueberry variety 'FC11-118' was initially crossed in 2007 in Lowell, Oreg., USA and planted in 2008 in a seedling plot where it was selected in 2011.

'FC11-118' was selected in 2011 for its exceptional fruit quality. It was further advanced and ultimately released because of the reliably high yields, superior fruit quality and storability, and exceptionally uniform, vigorous plants.

SUMMARY OF THE INVENTION

The new blueberry plant variety 'FC11-118' has not been observed under all possible environmental conditions. The phenotype may vary somewhat with variations in environment and cultural practices such as temperature and light intensity without, however, any variance in genotype.

The following characteristics of the new cultivar have been repeatedly observed and are determined to be the unique characteristics of the new blueberry plant variety 'FC11-118':

1) Extremely uniform healthy plant condition, vigor, and shape
2) Large, uniform fruit size and distinct fruit shape
3) Firm fruit texture
4) Excellent long-term cold storage performance

BRIEF DESCRIPTION OF THE DRAWINGS

The accompanying photographic illustration shows typical specimens in full color of the foliage and fruit of the new variety 'FC11-118'. The colors are as nearly true as is reasonably possible in a color representation of this type.

Figure 1:
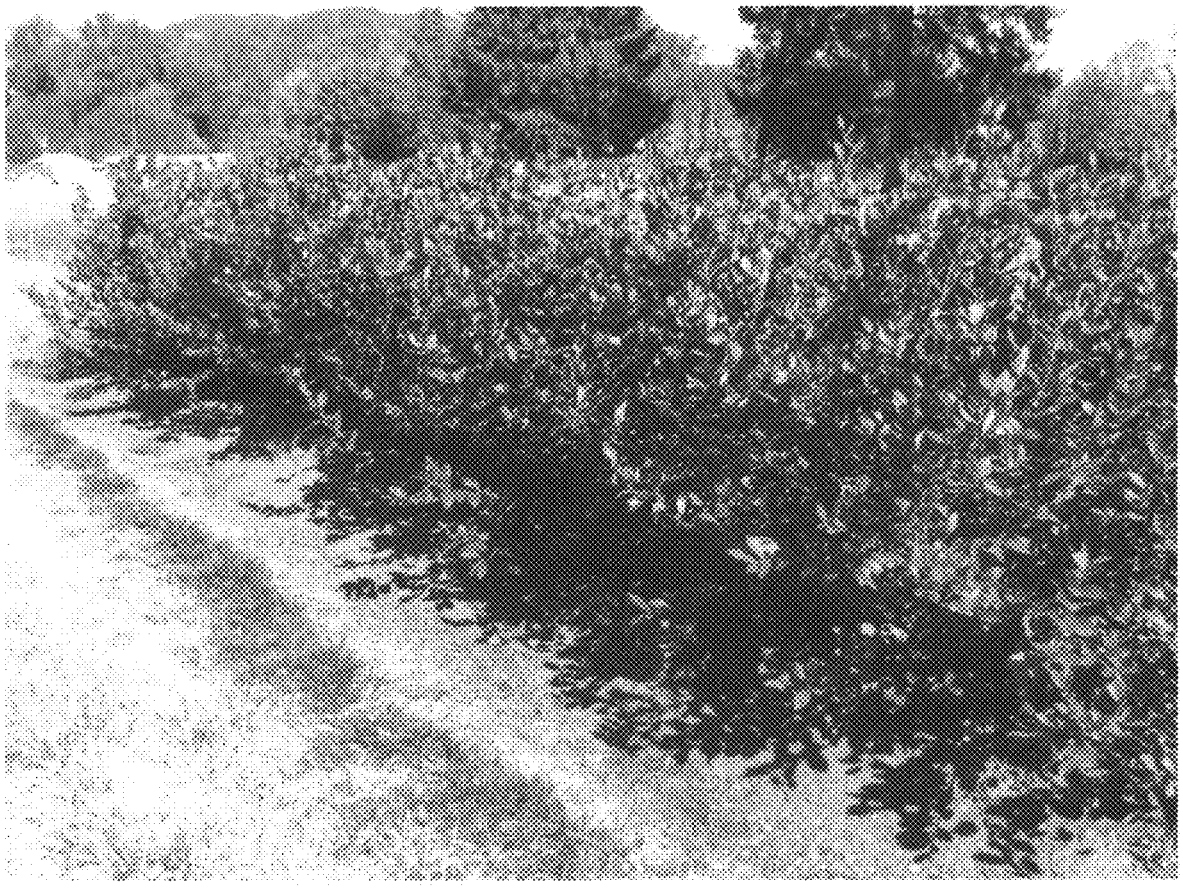
FIG. 1 is a photograph of the new variety 'FC11-118', demonstrating the plant's leaves and growth habit in the fall. The plants were grown in Lowell, Oreg. and photographed on Nov. 15, 2017.
Figure 2:
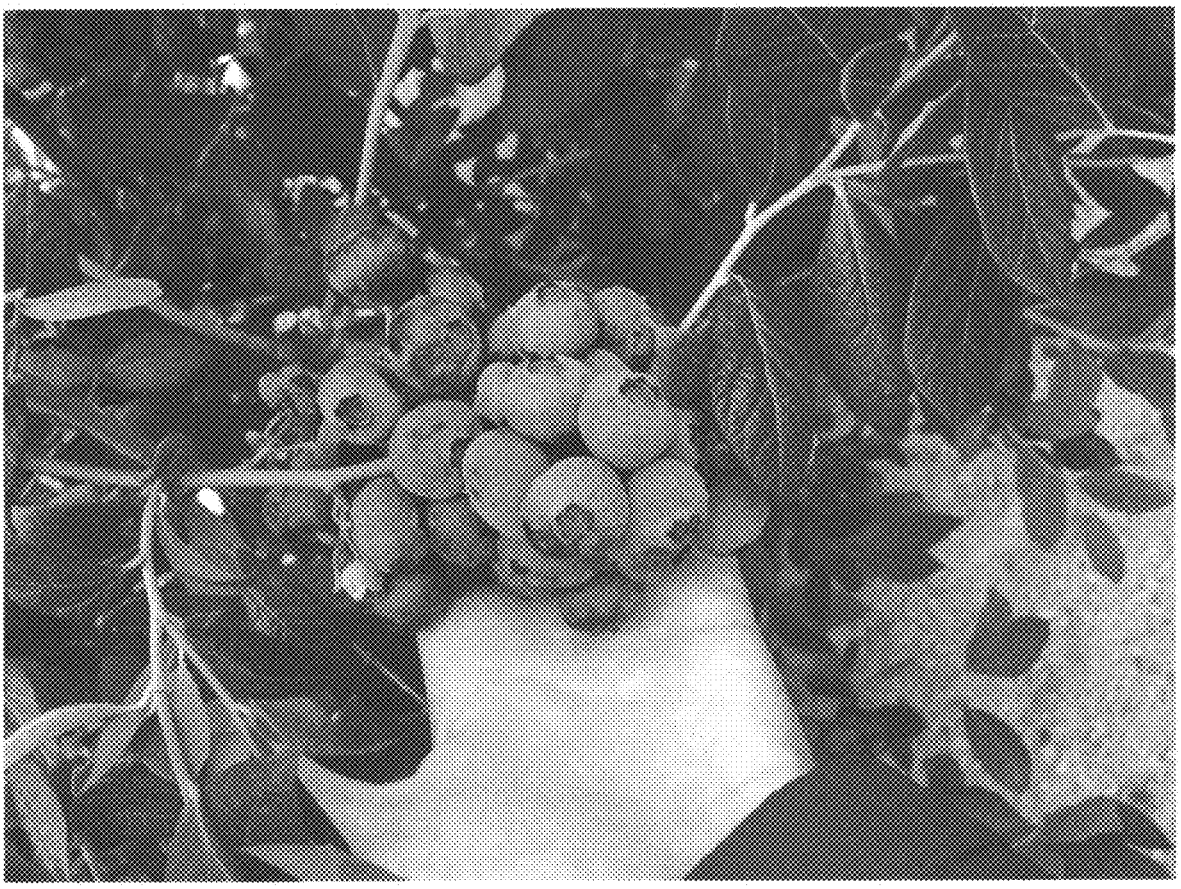
FIG. 2 is a photograph of the fruit cluster of the new variety 'FC11-118' grown in Lowell, Oreg. and photographed on Apr. 18, 2018.
Figure 3:
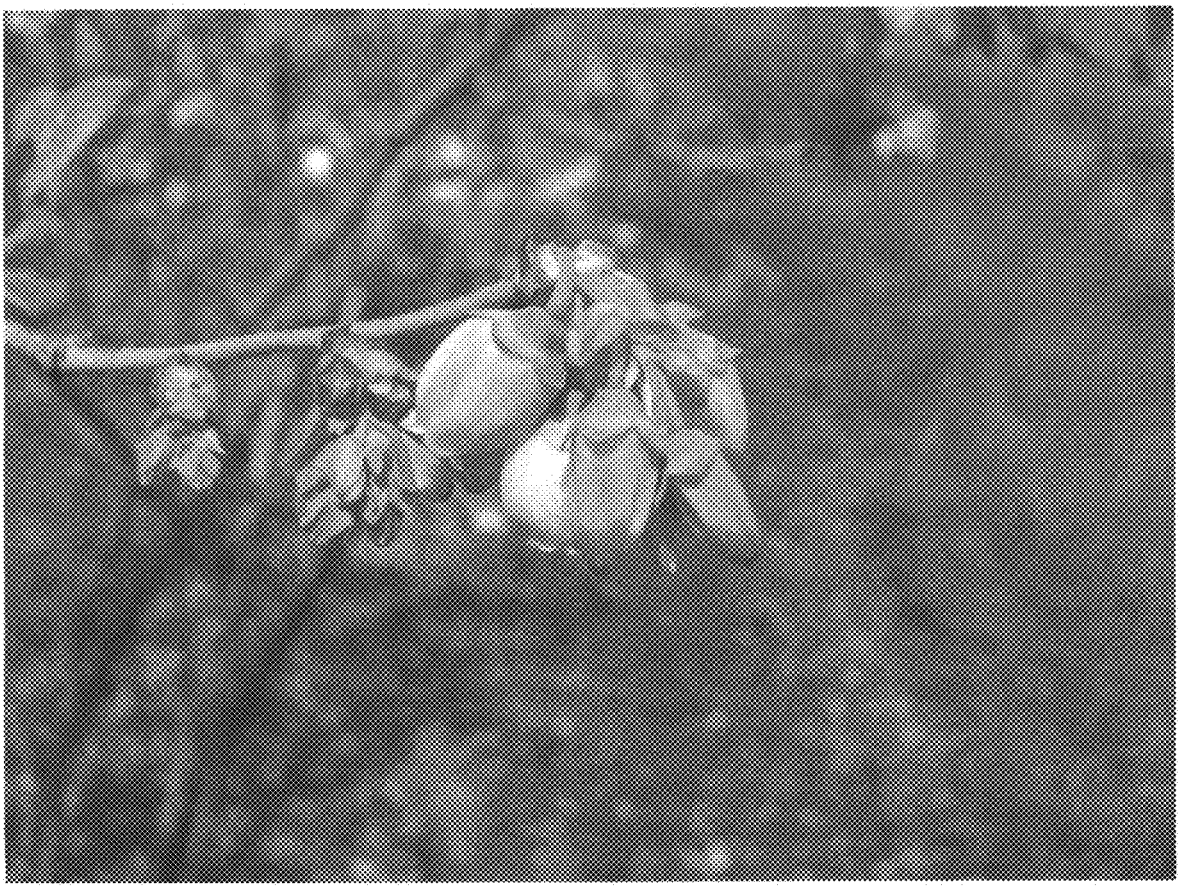
FIG. 3 is a photograph of the flowers of the new variety 'FC11-118' grown in Lowell, Oreg. and photographed on Apr. 18, 2018.
Figure 4:
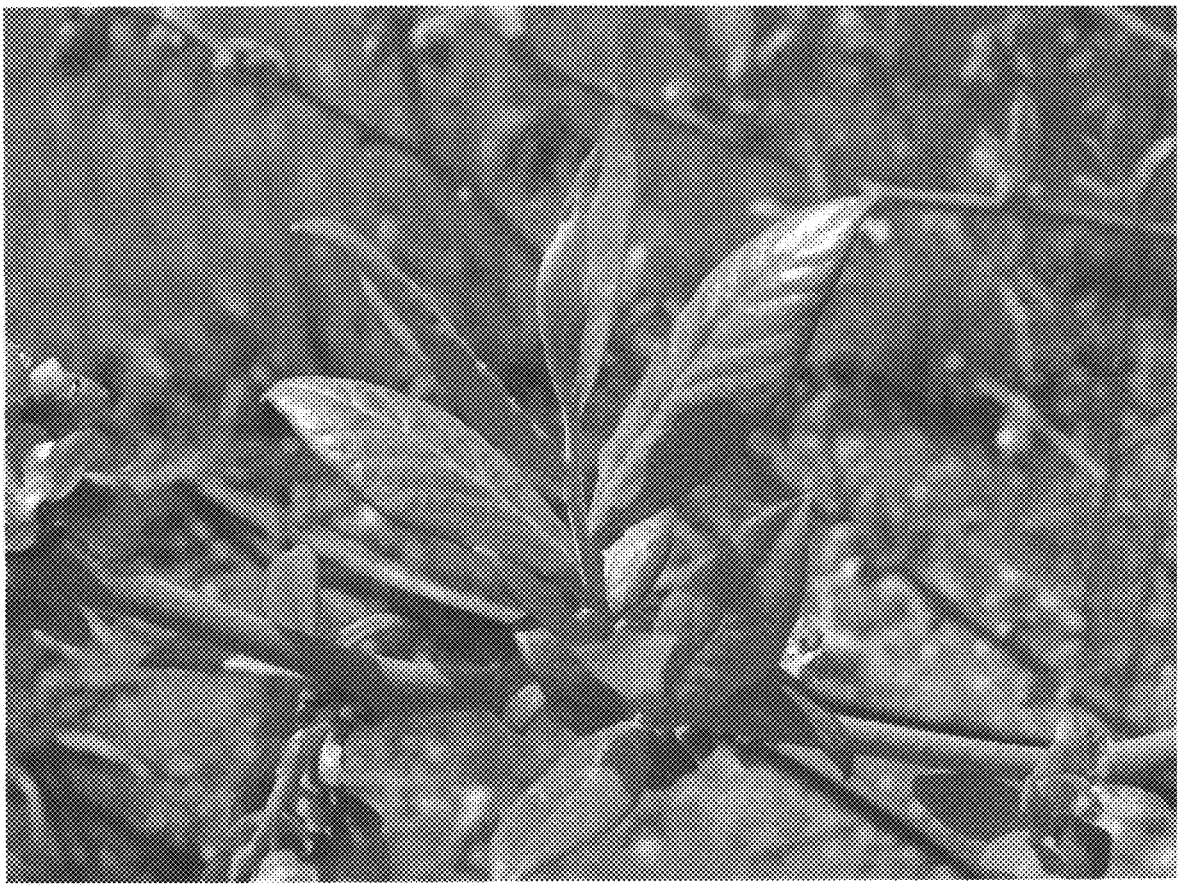
FIG. 4 is a photograph of the fall foliage of the new variety 'FC11-118' grown in Lowell, Oreg. and photographed on Nov. 17, 2018.
Figure 5:
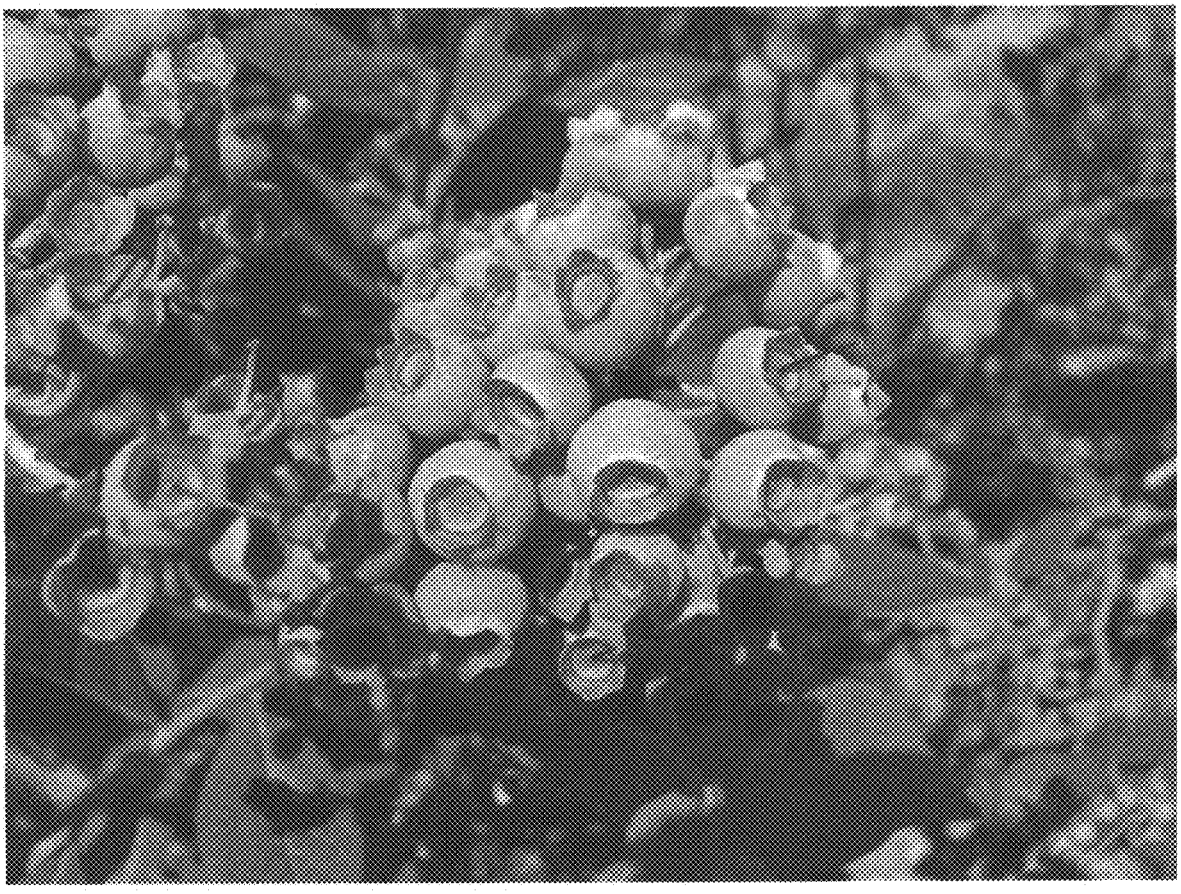
FIG. 5 is a photograph of immature fruit of the new variety 'FC11-118' grown in Lowell, Oreg. and photographed on May 22, 2018.
Figure 6:
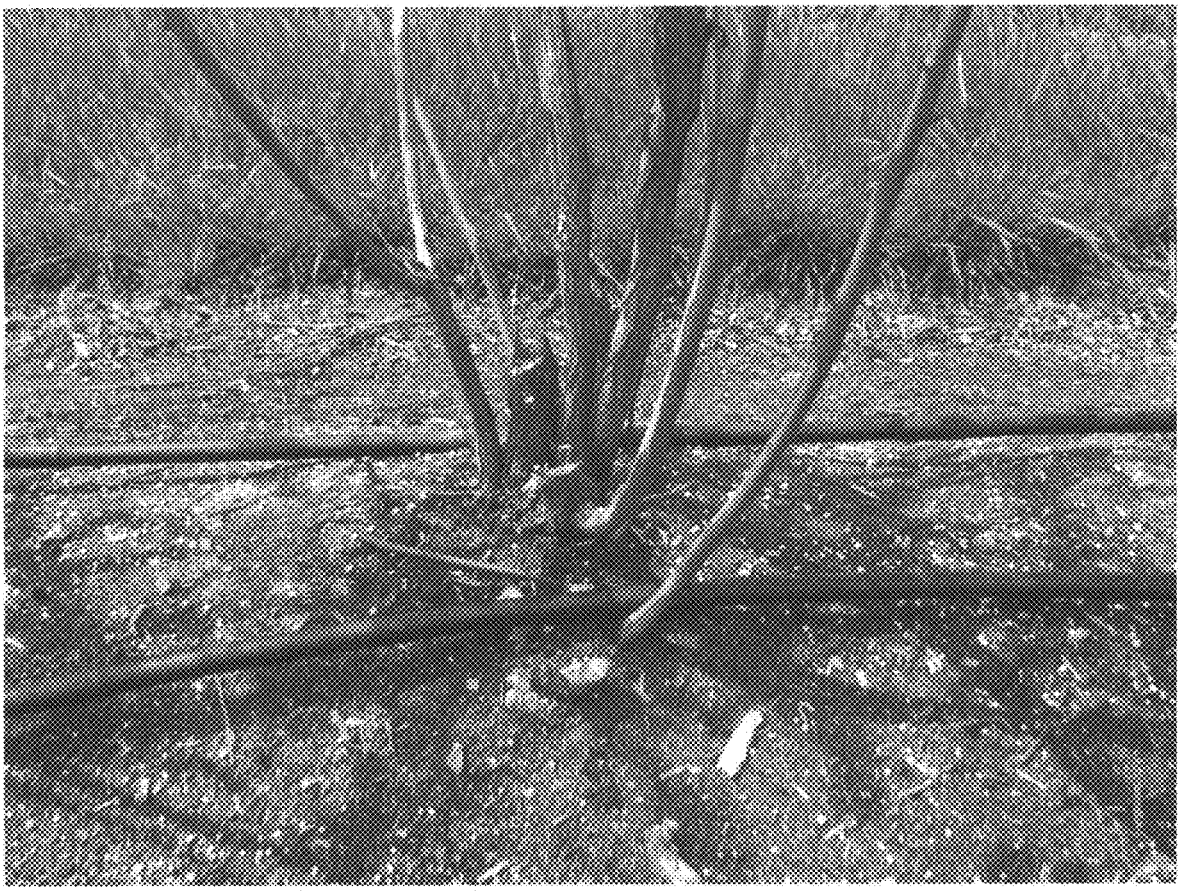
FIG. 6 is a photograph of one-year old canes on the new variety 'FC11-118' grown in Lowell, Oreg. and photographed on Apr. 18, 2018.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'FC11-118'. The data which defines these characteristics was collected from asexual reproductions of the original selection. Dimensions, sizes, colors, and other characteristics are approximations and averages set forth as accurately as possible. The plant history was taken on plants approximately 6 to 7 years of age, and the descriptions relate to plants grown in the field located at 39252 Jasper-Lowell Road, Lowell, Oreg., USA. Descriptions of fruit characteristics were made on fruit grown at the field described above. Color designations are from "The Pantone Book of Color" (by Leatrice Eiseman and Lawrence Herbery, Harry N. Abrams, Inc., Publishers, New York 1990). Where the Pantone color designations differ from the colors of the photographs, the Pantone colors are accurate.

Classification:

a. *Family*.—Ericaceae.
b. *Genus*.—*Vaccinium*.
c. *Species*.—*Corymbosum* hybrid.
d. *Common name*.—Northern Highbush Blueberry.

Parentage: Female Parent — 'ZF05-086' (unpatented). Male Parent — 'Cargo' (U.S. Plant Pat. No. 24,661 patented Jul. 22, 2014).

Market class: Hand harvest fresh market.

PLANT

General:

a. *Parentage*.—Female Parent — 'ZF05-086' (unpatented). Male Parent — 'Cargo' (U.S. Plant Pat. No. 24,661 patented Jul. 22, 2014).
b. *Plant height*.—Average 1.23 m.
c. *Plant width*.—Average 1.85 m.
d. *Growth habit*.—Round.
e. *Amount of growth in a season* (*i.e., plant vigor*).—High.
f. *Productivity*.—High. In Lowell, Oreg. on 3-year-old plants 5.0 lbs. per plant compared to 5.6 lbs per plant on Legacy.
g. *Cold hardiness*.—Good. In Central and Northwest Washington, there has been no cold damage.
h. *Chilling requirement*.—Estimated minimum of 800-1000.
i. *Leafing*.—Very good. Leaf to fruit ratio is balanced.
j. *Twigginess*.—Not very twiggy but with good amount of laterals.
k. *Resistance/susceptibility to root rot* (*phytopthora cinnamomii*).—Not overly susceptible.
l. *Resistance/susceptibility to stem blight* (*botryosphaeria sp.*) —Not overly susceptible.
m. *Resistance/susceptibility to Phomopsis twig blight* (*phomopsis vaccinii*).—Not overly susceptible.
n. *Resistance/susceptibility to botrytis* (*botrytis cinerea*).—Not overly susceptible.
o. *Resistance/susceptibility to leaf spot* (*septoria spp.*).—Not overly susceptible.
p. *Resistance/susceptibility to leaf rust* (*naohidemyces vaccinii*).—Not overly susceptible.
q. *Resistance/susceptibility to bud mites* (*acalatus vaccinii*).—Not overly susceptible.

STEM

General:

a. *Suckering tendency*.—Moderate (high for Northern Highbush but not as high as rabbiteye).
b. *Mature cane color*.—Pantone color 14-0708 (Cement).
c. *Mature cane length*.—Average 132.1 cm.
d. *Mature cane width*.—Average 15.569 mm.
e. *Bark texture*.—Rough.
f. *Fall color on new shoots*.—Pantone color 18-3415 (Grape Jam).
g. *Surface texture of new wood*.—Smooth.
h. *Internode length on strong, new shoots*.—20.876 mm.
i. *Average number of buds per fruiting lateral*.—5.2.

FOLIAGE

General:

a. *Time of beginning of leaf bud burst*.—Mid-April.
b. *Leaf color* (*top side*).—Pantone color 19-0323 (Chive).
c. *Leaf color* (*under side*).—Pantone color 17-0525 (Mosstone).
d. *Leaf arrangement*.—Alternate and Spirally: dextrose.
e. *Leaf shape*.—Elliptic.
f. *Leaf margins*.—Entire.
g. *Undulation of margin*.—None.

h. *Leaf venation*.—Anastomosing.
i. *Leaf apices*.—Acute.
j. *Leaf bases*.—Obtuse.
k. *Leaf length*.—Average 68.989 mm.
l. *Leaf width*.—Average 34.047 mm.
m. *Leaf length/width ratio*.—2.03.
n. *Leaf nectarines*.—Absent.
o. *Pubescence of upper side*.—Absent.
p. *Pubescence of lower side*.—Absent.
q. *Cross sectional profile*.—Revolute.
r. *Longitudinal profile*.—Plane.
s. *Attitude*.—Porrect.
t. *Fall foliage leaf color* (*top side*).—Pantone color 18-3415 (Grape Jam).

Petioles:
a. *Length*.—Average 4.132 mm.
b. *Width*.—Average 1.991 mm.
c. *Color*.—Pantone color 18-1741 (Raspberry Wine).
d. *Petiole surface texture*.—Smooth.

FLOWERS

General:
a. *Time of beginning of flowering*.—Approximately mid to late April in Lowell, Oreg.
b. *Time of* 50% *anthesis*.—Approximately late April in Lowell, Oreg.
c. *Flower shape*.—Cupuliform.
d. *Flower bud density*.—Medium.
e. *Flower fragrance*.—Faint to none.
f. *Immature flower color*.—Pantone color 15-1922 (Geranium Pink).
g. *Self-compatibility*.—Fair. Approximately 52% of self-pollinated flowers produced fruit compared to 72% of cross pollinated flowers.

Corolla:
a. *Color*.—Pantone color 11-0603 (Pastel Parchment).
b. *Length*.—Average 9.411 mm.
c. *Width*.—Average 8.022 mm.
d. *Aperture width*.—Average 3.971 mm.
e. *Anthocyanin coloration of corolla*.—Low-None; Pantone color 12-1304 (Pearl).
f. *Corolla ridges*.—Present.
g. *Protrusion of stigma*.—0.802 mm. below the corolla aperture.

Inflorescence:
a. *Length*.—Average 27.104 mm.
b. *Diameter*.—Average 29.702 mm.
c. *Length of peduncle*.—Average 14.770 mm.
d. *Surface texture of peduncle*.—Smooth.
e. *Color of peduncle*.—Pantone color 18-1629 (Faded Rose).
f. *Length of pedicel*.—Average 6.927 mm.
g. *Surface texture of pedicel*.—Smooth.
h. *Color of pedicel*.—Pantone color 16-1720 (Strawberry Ice).
i. *Number of flowers per cluster*.—Average 6.7.
j. *Flower cluster density*.—Medium.

Calyx (with sepals):
a. *Diameter*.—Average 7.342 mm.
b. *Color* (*sepals*).—Pantone color 12-0418 (Hay).

Stamen:
a. *Length*.—Average 6.992 mm.
b. *Number per flower*.—Average 10 stamen per flower.
c. *Filament color*.—Pantone color 12-0315 (White Jade).

Pistil:
a. *Length*.—Average 9.619 mm.
b. *Ovary color* (*exterior*).—Pantone color 17-0123 (Stone Green).
c. *Style length*.—Average 8.789 mm.

Anther:
a. *Length*.—Average 4.025 mm.
b. *Number*.—2 per filament.
c. *Color*.—Pantone color 17-1340 (Adobe).

Pollen:
a. *Abundance*.—Moderate.
b. *Color*.—Pantone color 12-0817 (Cornhusk).

FRUIT

General:
a. *Time of fruit ripening*.—Medium late. First harvest around the 3$^{rd}$ week of July in Lowell, Oreg.
b. *Time of* 50% *maturity*.—Approximately the middle of July in Lowell, Oreg.
c. *Fruit development period*.—Averaging 77 days in Lowell, Oreg.
d. *Mean harvest date*.—July 26$^{th}$.
e. *Mean date last pick*.—August 9$^{th}$.
f. *Cluster density*.—Medium.
g. *Berries per cluster*.—Average 7.4 berries per cluster.
h. *Unripe fruit color*.—Pantone color 14-0445 (Bright Chartreuse).
i. *Ripe berry color*.—Pantone color 16-3919 (Purple Cloud).
j. *Berry skin color after polishing*.—Pantone Color 19-4013 (Dark Navy).
k. *Berry surface wax abundance*.—Medium.
l. *Berry flesh color*.—Pantone color 12-6204 (Silver Green).
m. *Berry weight*.—Average 3.1795 g.
n. *Berry height from calyx to scar*.—Average 13.192 mm.
o. *Berry diameter*.—Average 18.901 mm.
p. *Calyx aperture*.—Average 6.905 mm.
q. *Calyx depth*.—Average 1.033 mm.
r. *Pedicel length*.—Average 8.260 mm.
s. *Pedicel surface texture*.—Smooth.
t. *Berry detachment force*.—Medium-easy.
u. *Berry shape*.—Oblate.
v. *Fruit stem scar*.—1.569 mm.
w. *Sweetness when ripe*.—Medium.
x. *Firmness when ripe*.—Very High.
y. *Acidity when ripe*.—Medium.
z. *Storage quality*.—Excellent at 42 days normal cold storage at +/−1C.

SEED

General:
a. *Seed abundance in fruit*.—Low-Average.
b. *Seed color*.—Pantone color 17-1134 (Brown Sugar).
c. *Seed dry weight*.—0.267 mg. per seed.
d. *Seed length*.—Average 1.500 mm.

COMPARISON BETWEEN PARENTAL AND COMMERCIAL CULTIVARS

TABLE 1

| Denomination of similar variety | Characteristic for comparison | State of expression of similar variety | State of expression of candidate variety 'FC11-118' |
|---|---|---|---|
| 'Cargo'(U.S. Plant Patent No. 24,661) | Leaf-fruit balance | Low | High |
| 'Cargo'(U.S. Plant Patent No. 24,661) | Firmness | Firm (283 g/mm) | Very Firm (315 g/mm) |

TABLE 1-continued

| Denomination of similar variety | Characteristic for comparison | State of expression of similar variety | State of expression of candidate variety 'FC11-118' |
|---|---|---|---|
| 'Legacy' | Fruit size | Large (1.8 g) | Very large (3.17 g) |
| 'Legacy' | Harvest concentration | 3 Harvests | 2 Harvests |
| 'ZF05-086' | Storability | Fair | Excellent |

The invention claimed is:

1. A new and distinct variety of blueberry plant named 'FC11-118', substantially as illustrated and described herein.

* * * * *